United States Patent [19]

Crawford

[11] Patent Number: 5,251,128
[45] Date of Patent: Oct. 5, 1993

[54] MOTION ARTIFACT REDUCTION IN PROJECTION IMAGING

[75] Inventor: Carl R. Crawford, Milwaukee, Wis.

[73] Assignee: General Electric Company, Milwaukee, Wis.

[21] Appl. No.: 615,778

[22] Filed: Nov. 19, 1990

[51] Int. Cl.[5] .............................................. G06F 15/42
[52] U.S. Cl. ........................... 364/413.19; 364/413.13
[58] Field of Search ..................... 364/413.13, 413.14, 364/413.16, 413.17, 413.19, 413.21; 378/901, 94; 128/653.1, 653.2

[56] References Cited

U.S. PATENT DOCUMENTS

| | | | |
|---|---|---|---|
| 4,144,569 | 3/1979 | Wagner | 364/413.16 |
| 4,272,820 | 6/1981 | Lux | 364/413.19 |
| 4,387,722 | 6/1983 | Kearns | 128/716 |
| 4,570,224 | 7/1986 | Shimoni et al. | 364/413.16 |
| 4,614,195 | 9/1986 | Bottomley et al. | 128/653.2 |
| 4,682,109 | 7/1987 | Cuppen | 324/309 |
| 4,703,424 | 10/1987 | Gullberg et al. | 364/413.21 |
| 4,712,560 | 12/1987 | Schaefer et al. | 128/653.2 |
| 4,779,620 | 10/1988 | Zimmermann et al. | 128/653.2 |
| 4,812,983 | 3/1989 | Gullberg et al. | 364/413.17 |
| 4,855,910 | 8/1989 | Bohning | 364/413.13 |
| 4,930,508 | 6/1990 | Shimoni et al. | 128/653.1 |
| 4,937,526 | 6/1990 | Ehman et al. | 324/309 |
| 4,994,965 | 2/1991 | Crawford et al. | 364/413.15 |
| 5,032,990 | 7/1991 | Eberhard et al. | 364/413.15 |
| 5,035,244 | 7/1991 | Stokar | 128/653.1 |
| 5,056,020 | 10/1991 | Feldman et al. | 364/413.19 |

OTHER PUBLICATIONS

Gullberg, Grant T., Crawford, Carl R., and Tsui, Benjamin M. W., "Reconstruction Algorithm for Fan Beam with a Displaced Center-of-Rotation", *IEEE Transactions on Medical Imaging*, vol. MI-5, Mar. 1986.

Crawford, Carl R., Gullberg, Grant T., and Tsui, Benjamin, "Reconstruction for Fan Beam with an angular-dependent displaced center-of rotation", *Med. Phys 15(1)* Jan./Feb. 1988.

Primary Examiner—Roy N. Envall, Jr.
Assistant Examiner—David Huntley
Attorney, Agent, or Firm—Quarles & Brady

[57] ABSTRACT

An x-ray CT scanner acquires projection data from a series of views during a scan of a patient's chest. Movement of the patient's chest due to respiration is also sensed during the scan and this acquired motion data is employed along with a geometric model of chest motion to calculate factors which correct the acquired projection data and reduce motion artifacts in an image produced by back projecting the acquired projection data.

10 Claims, 5 Drawing Sheets

MOTION ARTIFACT REDUCTION IN PROJECTION IMAGING

BACKGROUND OF THE INVENTION

The present invention relates to medical imaging, and particularly, to the reduction of motion artifacts in images produced using a projection method of reconstruction.

There are a number of modalites used to produce medical images. These include x-ray computed tomography (CT), magnetic resonance imaging (MRI), single photon emission computed tomography (SPECT), and positron emission computed tomography (PET) methods. In all cases, the data used to reconstruct the desired image is acquired over a period of time in a scan comprised of a series of views. Each view is a snapshot of the patient from a different angle, or perspective, and a scan typically includes tens, or hundreds of views. In the case of x-ray CT the entire data set may be acquired in a few seconds, whereas an MRI scan typically requires a few minutes to complete. The methods used to reconstruct an image from such data sets presume that the patient is motionless during the entire scan and that the same fixed object is the subject of all acquired views. To the extent this is not true, artifacts such as ghosts, smearing and fuzziness appear in the reconstructed image.

Efforts to reduce patient motion during a scan can significantly improve image quality. However, artifacts caused by respiration is a significant problem in chest scans where suspension of breathing is not possible or poor instructions are provided to the patient by the scanner operator. Children and comatose patients are routinely scanned with no attempt to synchronize respiration with scanning, and it is expected in such cases that a number of poor quality images will be produced and will be discarded.

One approach to reducing motion artifacts in medical images is to retrospectively correct the acquired data to offset the affects of motion. One such method, for example, is disclosed in U.S. Pat. No. 4,937,526 and is applied to acquired MRI data. The corrections that are made may be determined from an examination of the acquired raw data itself, or additional information, such as a signal from a cardiac monitor or a respiration monitor, may be used. The manner in which the corrections are made to the acquired raw data is determined by the particular reconstruction technique that is used. In the above patent, for example, a 2D Fourier transformation is used to reconstruct an image from the acquired MRI data, and the correction methods disclosed are limited to that technique.

The back projection method for image reconstruction is employed to some extent in all computed medical imaging modalites. It is the predominant method used in x-ray CT, and there is a need to correct acquired data used in projection imaging for the effects of patient motion.

SUMMARY OF THE INVENTION

The present invention relates to a method for correcting data used to reconstruct medical images using a back projection technique, and particularly, to a method for reducing artifacts in the reconstructed image due to respiratory motion of the patient during the data acquisition. More specifically, the method includes acquiring the image data during a scan comprised of a series of views, acquiring motion data with each view that measures a parameter associated with patient respiration, correcting the acquired image data as a function of the acquired motion data and a geometric model of the patient's chest cavity during respiration, and reconstructing an image by back projecting the corrected acquired image data.

A general object of the invention is to reduce artifacts produced in back projection images caused by patient respiration. A model of how the patient's chest changes in size and shape as a function of a measured parameter has been developed. By acquiring the measured parameter along with each view in the scan, the size and shape of the patient's chest as seen by each view can be determined. During the reconstruction, the acquired data is first corrected by a weighting factor and is then used in a back projection process which "sees" the patient's chest in a single reference position.

A more specific object of the invention is to provide a method for weighting image data acquired by an x-ray CT and reconstructing an image from the weighted image data using a back projection technique. The back projection process is altered by a displacement factor to properly reconstruct the image and the specific weighting factors and displacement factors for both parallel beam and fan-beam CT scanners have been developed.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
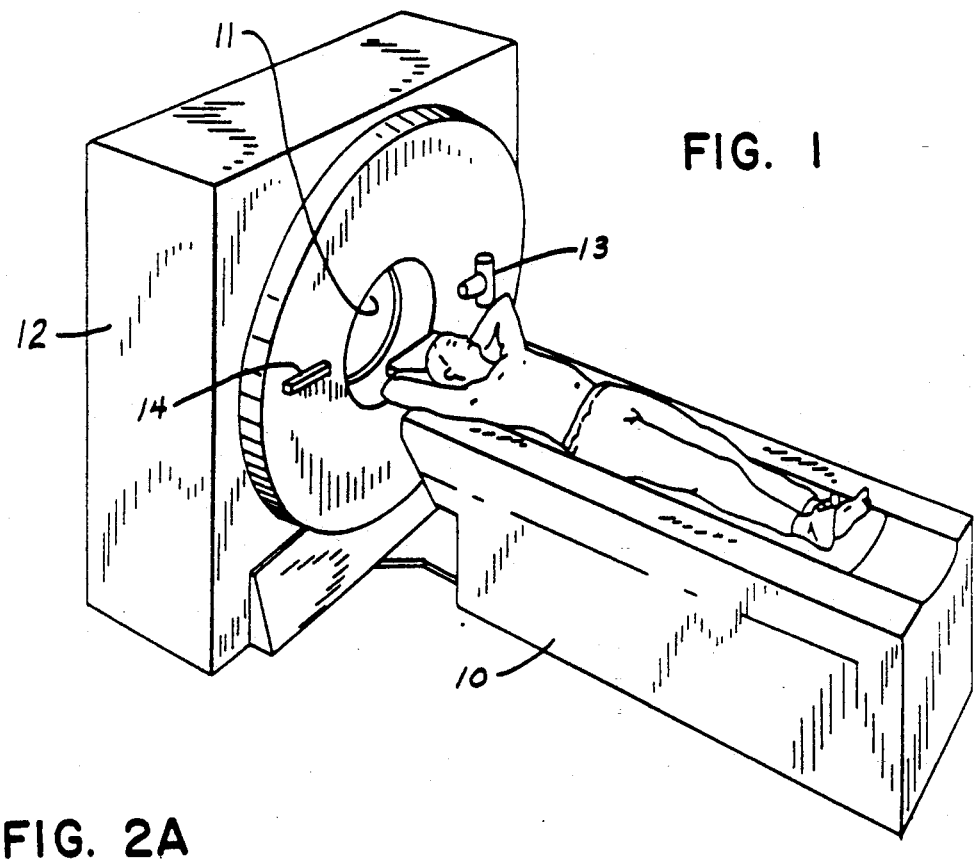
FIG. 1 is a perspective view of an x-ray CT scanner and patient.

While the present invention may be applied to many different imaging systems that employ back projection image reconstruction methods, the preferred embodiment is employed in an x-ray CT scanner such as that illustrated in FIG. 1.

As shown in FIG. 1, a CT scanner used to produce images of the human anatomy includes a patient table 10 which can be positioned within the aperture 11 of a gantry 12. A source of highly columinated x-rays 13 is mounted within the gantry 12 to one side of its aperture 11, and one or more detectors 14 are mounted to the other side of the aperture. The x-ray source 13 and detectors 14 are revolved about the aperture 11 during a scan of the patient to obtain x-ray attenuation measurements from many different angles.

Figure 2A:
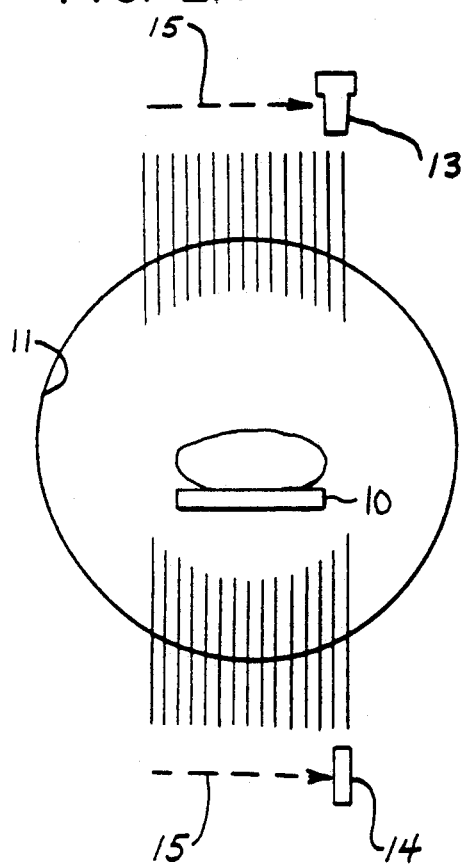
FIGS. 2A and 2B are schematic drawings of a parallel beam and a fan-beam scanning assembly on the scanner of FIG. 1.
Figure 2B:
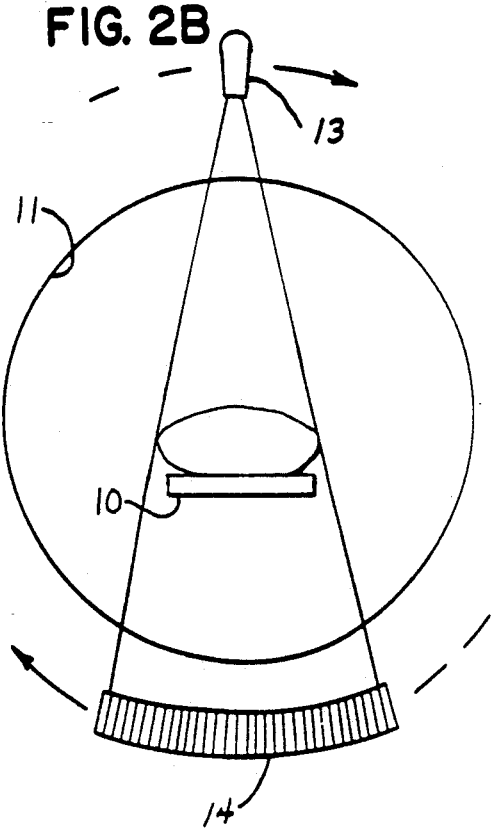

A complete scan of the patient is comprised of a set of x-ray attenuation measurements which are made at discrete angular orientations of the x-ray source 13 and detector 14. Each such set of measurements is referred to in the art as a "view" and the results of each such set of measurements is a transmission profile, or projection. As shown in FIG. 2A, the set of measurements in each view may be obtained by simultaneously translating the x-ray source 13 and detector 14 across the acquisition field of view, as indicated by arrows 15. As the devices 13 and 14 are translated, a series of x-ray attenuation measurements are made through the patient and the resulting set of data provides a transmission profile at one angular orientation ($\theta$). The angular orientation of the devises 13 and 14 is then changed (for example, 1°) and another view is acquired. These are known in the art as parallel beam projections. An alternative structure for acquiring each transmission profile is shown in FIG. 2B. In this construction, the x-ray source 13 produces a fan-shaped beam which passes through the patient and impinges on an array of detectors 14. The detectors 14 can be curved as shown in FIG. 2B, or they can be aligned in a straight line (not shown in the drawings). Each detector 14 in this array produces a separate attenuation signal and the signals from all the detectors 14 are separately acquired to produce the transmission profile for the indicated angular orientation. As in the first structure, the x-ray source 13 and detector array 14 are then rotated to a different angular orientation and the next transmission profile is acquired.

As the data is acquired for each transmission profile, the signals are filtered, corrected and digitized for storage in a computer memory. These steps are referred to in the art collectively as "preprocessing" and they can be performed in real time as the data is being acquired. The acquired transmission profiles are then used to reconstruct an image which indicates the x-ray attenuation coefficient of each voxel in the reconstruction field of view. These attenuation coefficients are converted to integers called "CT numbers", which are used to control the brightness of a corresponding pixel on a CRT display. An image which reveals the anatomical structures in a slice taken through the patient is thus produced.

Figure 3:
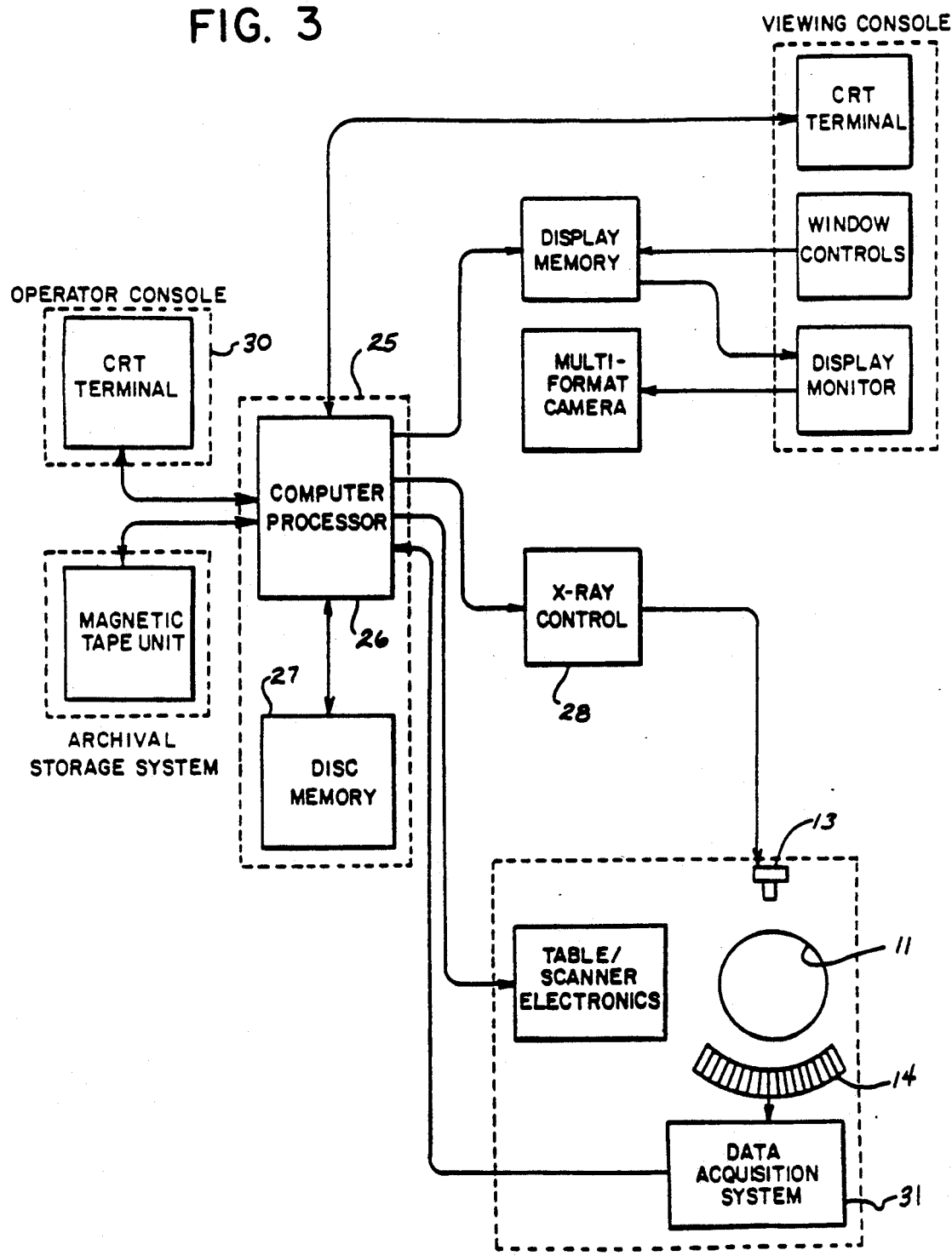
FIG. 3 an electrical block diagram of the scanner of FIG. 1.

Referring particularly to FIG. 3, the operation of the CT system is controlled by a programmed data processing system 25 which includes a computer processor 26 and a disc memory 27. The disc memory 27 stores the programs the computer processor 26 uses in patient scanning and in image reconstruction and display. It also stores on a short-term basis the acquired data and the reconstructed image data. The computer processor includes a general purpose minicomputer with input and output ports suitable for connection to the other system elements as shown. It also includes an array processor such as that disclosed in U.S. Pat. No. 4,494,141 which is encorporated herein by reference.

An output port on the computer processor 26 connects to an x-ray control circuit 28, which in turn controls the x-ray tube 13. The high voltage on the x-ray tube 13 is controlled and its cathode current is controlled to provide the correct dosage. The high voltage and cathode current are selected by an operator who enters the desired values through an operator console 30 and the computer processor 26 directs the production of the x-rays in accordance with its scan program.

The x-rays are dispersed in a fan-shape as described above and received by the array of detectors 14 mounted on the opposite side of the gantry aperture 11. Each individual cell, or detector element, examines a single ray originating from the x-ray tube 13 and traversing a straight line path through a patient located in the aperture 11. The currents formed in each detector element are collected as an analog electrical signal and converted into a digital number by A/D converters in a data acquisition system 31. The digitized measurements from all the detectors is a complete view. U.S. Pat. Nos. 4,112,303 and 4,115,695 disclose details of the gantry construction, U.S. Pat. No. 4,707,607 discloses the details of the detector array 14, and the data acquisition system is disclosed in U.S. Pat. No. 4,583,240. All of these patents are incorporated herein by reference. The digitized signals are input to the computer processor 26.

Figure 4:
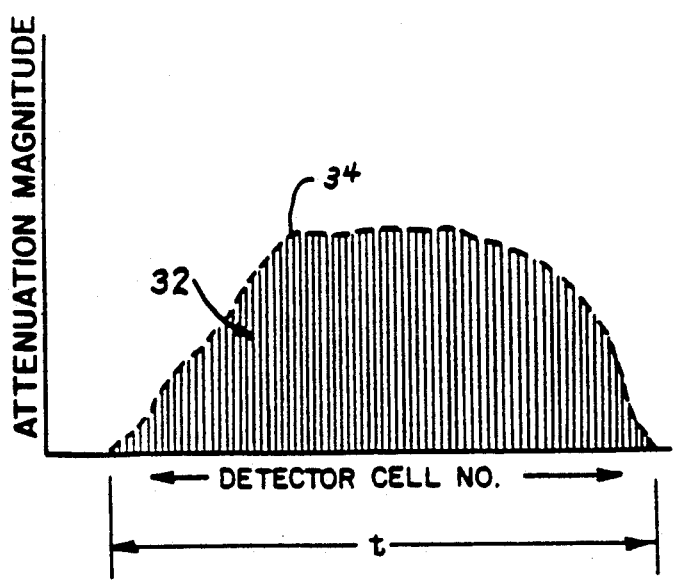
FIG. 4 is a graphic representation of one view of data acquired by the scanner of FIG. 1.

The digitized attenuation measurements from the data acquisition system 31 are preprocessed in a well-known manner to compensate for "dark currents", for uneven detector cell sensitivities and gains, and for variations in x-ray beam intensity throughout the scan. This is followed by beam hardening corrections and conversion of the data to logarithmic form so that each measured value represents a line integral of the x-ray beam attenuation. This preprocessing is performed in real time as the scan is being conducted, and as shown in FIG. 4, each view is comprised of a set of attenuation values 32 which define a transmission profile, or projection, indicated by dashed line 34.

In addition to the transmission profile data 34, two other pieces of information are input during the acquisition of each view. The first is the angle ($\theta$) which indicates the angular orientation of the x-ray source 13 and detectors 14 with respect to the vertical reference axis. Typically, for example, the views are acquired at 1° increments over a range of 180°.

Figure 5:
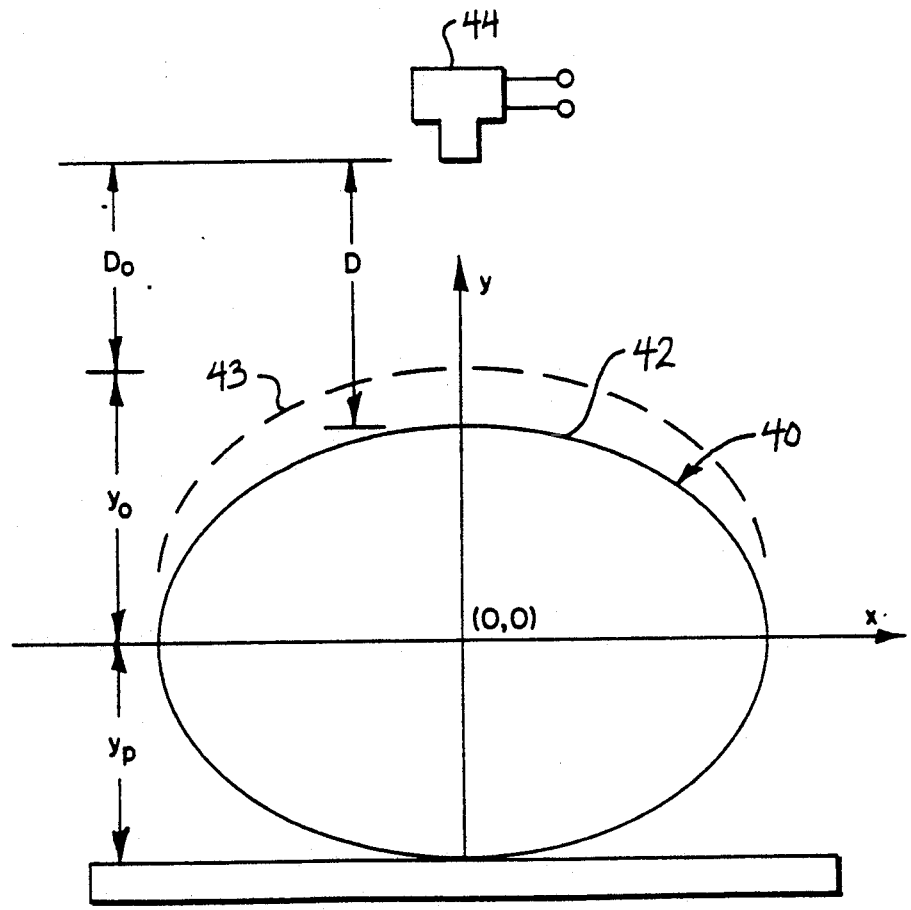
FIG. 5 is a schematic representation of a patient's chest cavity showing the orientation of a range finder that forms part of the scanner of FIG. 1.

The second piece of information acquired with each view is a distance value (D) that is indicative of the position of the patient's chest cavity and which is a parameter employed in a geometric model of the chest cavity during respiration. Referring particularly to FIG. 5, this geometric model is illustrated by a schematic cross-section taken in a transverse plane through the patient's chest as indicated at 40. As the patient breathes the posterior abdominal wall 41 which rests on the supporting table 10 does not move any significant amount, whereas the anterior abdominal wall 42 moves vertically as indicated by the dashed line 43. As will be described below, the size and shape of the patient's chest cavity at any point in the respiratory cycle can be approximated by monitoring the vertical position of the anterior wall 42. Accordingly, an ultrasonic range finder 44 is mounted to the gantry 12 and is positioned to measure the vertical distance (D) to the patient's chest. This measured (D) is input to the computer processor 26 (FIG. 3) along with each view of acquired data.

Referring still to FIG. 5, as the patient breathes and the anterior abdominal wall 42 moves up and down, the contents of the chest cavity magnify and shrink along the vertical axis (y). This magnification does not occur about the center near y=0, but instead, at the posterior wall 41 located at $y = -y_p$. There is virtually no magnification along the horizontal (x), but to the extent that there is, it occurs about the center of the chest cavity at x=0 (if the patient is centered on the table 10). Using this model and the measured parameter D, the present invention corrects the acquired projection data and employs the corrected projection data in the back projection reconstruction process such that the chest cavity appears stationary in a reference position during the entire scan. As a result, motion artifacts are significantly reduced or eliminated.

The corrections to the acquired data and the manner in which the corrected data is employed in the back projection process has been determined for a general case in which patient motion produces magnification along two axes (x and y) and the point about which magnification occurs is shifted, or offset, from the origin (x=0, y=0). The correction factors for this generalized case have been determined and will now be described.

Let f(x,y) be the cross-section of the patient which is to be reconstructed. A magnified and shifted version of this same cross-section during various stages of the respiratory cycle is given by:

$$f(x,y) = f(a_x + \beta_x x, a_y + \beta_y y) \qquad [1]$$

where $\beta_x$ and $\beta_y$ are modification factors along the respective x and y axes and $a_x$ and $a_y$ are shift factors. For parallel beam projection data the formula for projection of this magnified image at gentry rotational angle $\theta$ is given by:

$$p'(\theta,t) = \int_{-\infty}^{\infty} \int_{-\infty}^{\infty} f(x,y)\, \delta(t - x\cos\theta - y\sin\theta)\, dx\, dy \qquad [2]$$

where $\delta(t)$ is the Dirac-delta function known to those skilled in this art. The Fourier tranform of this projection can be found:

$$S'(\theta,\omega) = \int_{-\infty}^{\infty} f(a_x + \beta_x x, a_y + \beta_y y) e^{-j2\pi\omega(x\cos\theta + y\sin\theta)}\, dx\, dy \qquad [3]$$

Now make the following changes of variables $$x' = a_x + \beta_x x$$
$$y' = a_y + \beta_y y \qquad [4]$$

When [4] is used in [3], the following is obtained $$S'(\theta,\omega) = \qquad [5]$$

$$\int_{-\infty}^{\infty} \frac{f(x,y)}{\beta_x \beta_y} e^{-j2\pi\omega[\frac{x}{\beta_x}\cos\theta + \frac{y}{\beta_y}\sin\theta]} e^{j2\pi\omega[\frac{a_x}{\beta_x}\cos\theta + \frac{a_y}{\beta_y}\sin\theta]}\, dx\, dy$$

Let F(u,v) be the two-dimensional Fourier transform of f(x,y). Then it is seen that $$S'(\theta,\omega) = \frac{e^{j2\pi\omega[\frac{a_x}{\beta_x}\cos\theta + \frac{a_y}{\beta_y}\sin\theta]}}{\beta_x \beta_y} F\left[\frac{\omega\cos\theta}{\beta_x}, \frac{\omega\sin\theta}{\beta_y}\right] \qquad [6]$$

This equation is a version of the Fourier Slice Theorem in the case of projections acquired from a magnified and shifted object function. It says that the Fourier transform of the projection at gantry position $\theta$ is a spoke of the two-dimensional Fourier transform of the object function at angle $$\theta' = \tan^{-1}\left[\frac{\beta_x}{\beta_y}\tan\theta\right] \qquad [7]$$

after a phase term and a scaling factor have been removed.

Equations [6] and [7] could form the basis of a reconstruction algorithm which employs a two-dimensional Fourier transform of the data which results from the mapping of the one-dimensional Fourier transform of the projection data into the Fourier transform of the patient. This is not the preferred method of reconstruction. Instead, a filtered back projection method has been developed and will now be described in detail.

A filtered back projection reconstruction formula will now be derived for reconstructing f(x,y) using p'($\theta$,t). The inverse Fourier transform of F(u,v), is given by $$f(x,y) = \int_{-\infty}^{\infty} \int_{-\infty}^{\infty} F(u,v) e^{j2\pi(ux+vy)}\, du\, dv \qquad [8]$$

Consider the following change of variables $$u = \frac{\omega}{\beta_x}\cos\theta \qquad [9]$$

$$v = \frac{\omega}{\beta_y}\sin\theta$$

The components of the Jacobian in this change of variables are given by $$\frac{\partial u}{\partial \omega} = \frac{\cos\theta}{\beta_x} \qquad [10]$$

$$\frac{\partial u}{\partial \theta} = -\frac{\omega\sin\theta}{\beta_x} - \frac{\omega\beta'_x \cos\theta}{\beta_x^2}$$

$$\frac{\partial v}{\partial \omega} = \frac{\sin\theta}{\beta_y}$$

$$\frac{\partial v}{\partial \theta} = \frac{\omega\cos\theta}{\beta_y} - \frac{\omega\beta'_y \sin\theta}{\beta_y^2}$$

where $\beta'_x$ and $\beta'_y$ are the derivatives of $\beta_x$ and $\beta_y$ with respect to $\theta$. The Jacobian, $J(u,v,\omega,\theta)$, can be determined using [10] resulting in $$J(u,v,\omega,\theta) = |\omega| g(\theta) \qquad [11]$$

where $$g(\theta) = \left|1 + \frac{\sin 2\theta}{2}\left[\frac{\beta'_x}{\beta_x} - \frac{\beta'_y}{\beta_y}\right]\right| / \beta_x \beta_y \qquad [12]$$

The value $g(\theta)$ is a weighting factor which is applied to the projection data at gantry position $\theta$. In the parallel beam acquisition, this weighting factor is a constant value which is applied to each attenuation value 32 in the projection profile 34 at the position $\theta$ (FIG. 4). In some situations where the density of the object being imaged does not change as it is magnified, this weighting factor is modified to more closely approximate the geometric model of motion in equation [1]. More specifically, in such cases the weighting factor $g(\theta)$ should be multiplied by the value $\beta_y\beta_x$. The derivatives $\beta'_x$ and $\beta'_y$ can be calculated with numerical differences using the adjacent values of $\beta_x$ and $\beta_y$.

Using [9] and [11], [8] becomes $$f(x,y) = \int_0^\pi \int_{-\infty}^{+\infty} F\left[\frac{\omega \cos\theta}{\beta_x}, \frac{\omega \sin\theta}{\beta_y}\right] |\omega| g(\theta) e^{j2\pi\omega[\frac{x}{\beta_x}\cos\theta + \frac{y}{\beta_y}\sin\theta]} d\omega d\theta \quad [13]$$

When [6] is used, [13] reduces to $$f(x,y) = \int_0^\pi q_\theta\left(\left[\frac{(x-a_x)}{\beta_x}\right]\cos\theta + \left[\frac{(y-a_y)}{\beta_y}\right]\sin\theta\right) d\theta \quad [14]$$

where $$q_\theta(t) = \int_{-\infty}^{+\infty} S'(\theta,\omega) |\omega| g(\theta) e^{j2\pi\omega t} d\omega \quad [15]$$

Equation [14] represents a filtered back projection formula for reconstruction of parallel projections that are acquired from the magnified and shifted object. The formula is valid for reconstructing any point in the x-y plane.

The image f(x,y) can be reconstructed, therefore, from a set of parallel beam projections acquired over a range of 180° gantry positions by modifying the conventional data acquisition and reconstruction method in the following manner. First, for each projection of the patient, not only is the attenuation profile data acquired, but also, the parameters $\alpha_x$, $\beta_x$, $\alpha_y$ and $\beta_y$ are measured. In the preferred embodiment, $\alpha_x$ is set to zero and $\beta_x$ is set to one since the patient is usually centered on the table 10 and there is very little magnification of the chest cavity along the x axis during respiration. Only $\beta_y$ and $\alpha_y$ are required, therefore, to significantly reduce motion artifacts in the chest cavity and these are measured indirectly. As shown in FIG. 5, the distance between y=0 and the point about which magnification occurs is fixed at $-y_p$. Also, the distance between the range finder 44 and this same point is fixed. As a result, the values for $\beta_y$ and $\alpha_y$ can be calculated from these fixed values and the measurement (D) produced by the range finder 44 as follows:

$$\beta_y = 1/(1+(D-D_0)/(y_0+y_p)) \quad [16]$$

$$\alpha_y = -y_p(1-\beta_y) \quad [17]$$

where $y_0$ is a reference position for the anterior chest wall which is selectable by the operator and which determines the shape and size of the reconstructed image, and $D_0$ is the range finder measurement at this reference position. Consequently, the distance measurement (D) is acquired along with each projection profile and this measured parameter is sufficient to indicate the shape and size of the patient's chest cavity at the moment the view was acquired.

The preferred embodiment of the invention will now be described with reference to the flow chart of FIG. 6. While most of the steps are carried out in dedicated hardware so that the processing can be carried out in "real time", the process itself is controlled by a program executed by the computer 26 which performs the scan.

This control program is entered at 75 and the CT system is initialized at process block 76 to acquire the data for the first view. This includes receiving input data from the operator such as the reference chest position $y_0$ and reference range finder distance $D_0$, and orientation of the gantry to the desired starting position of $\theta = -90°$. A loop is then entered in which the profile data for the first view is acquired and preprocessed as indicated at block 77. The distance measurement (D) from the range finder 44 (FIG. 5) is acquired at process block 78 and the values for $\beta_y$ and $\alpha_y$ are calculated at process block 79 using the equations [16] and [17]. The acquired projection data is filtered in the usual fashion at process block 80 and then it is weighted at process block 81 by multiplying each value in the profile data set by the weighting factor $g(\theta)$ calculated in accordance with equation [12].

Figure 7:
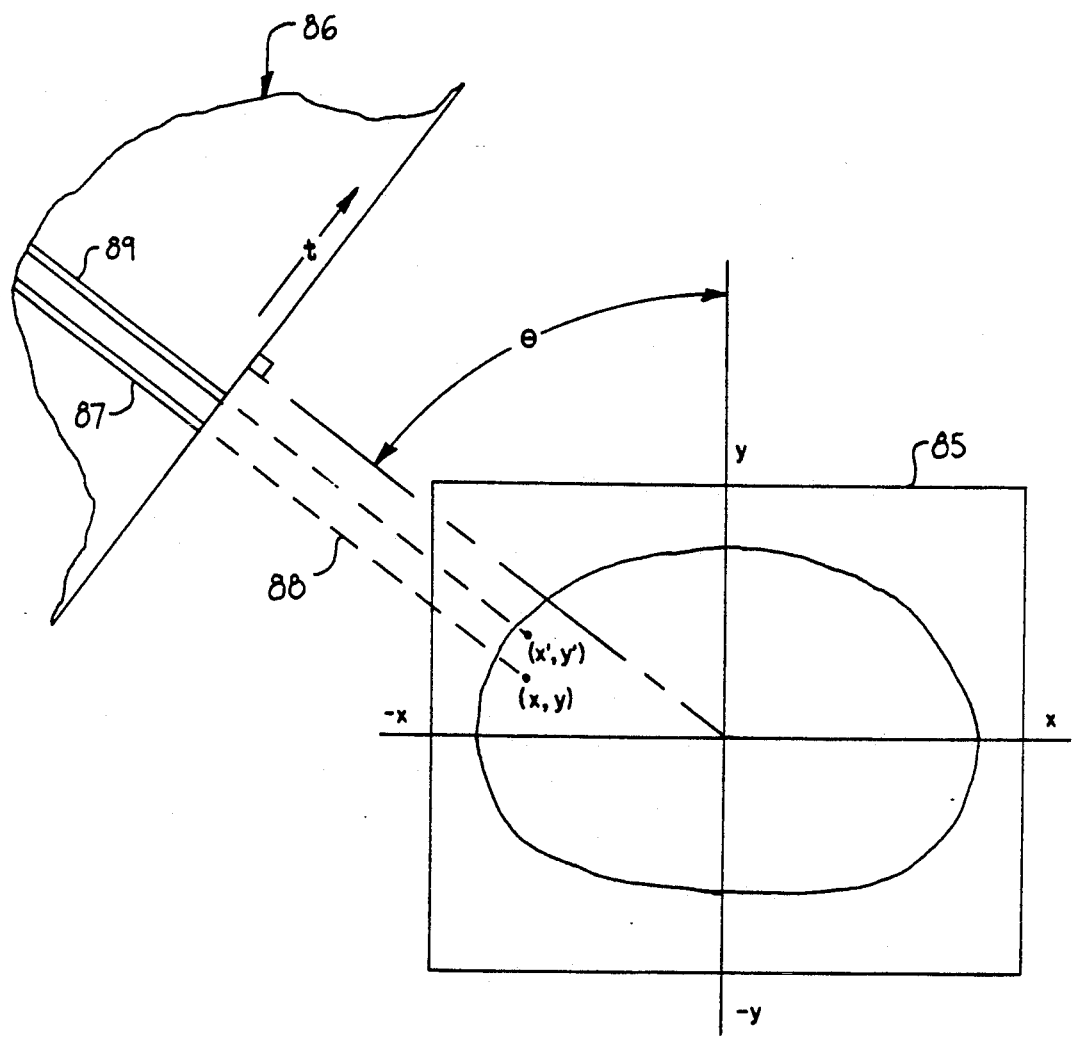
FIG. 7 is a schematic representation of one of the steps employed by the program of FIG. 6.

The corrected projection data is employed in reconstructing an image using the back projection technique as indicated at process block 82. As indicated by equation [14], however, this process is modified to account for motion. Referring particularly to FIG. 7, a 512 by 512 pixel image 85 is created by determining which of the values in the corrected and filtered projection data set 86 contribute to the brightness value of the pixel located at (x,y). In a parallel beam acquisition the conventional back projection formula for determining which value (t) to use is as follows:

$$t = x \cos\theta + y \sin\theta \quad [18]$$

where (x,y) is the location of the pixel, $\theta$ is the projection angle for the view, and t is the location in the projection data set from which an attenuation value 87 is read. This standard back projection is shown in FIG. 7 by the dashed line 88. Typically, t is located between two samples in the acquired data set and interpolation is used to determine a more accurate value to be added to the CT number for pixel (x,y). For each projection, all of the pixels in the image 85 are processed in this fashion to determine the contribution to their accumulated CT numbers.

To practice the present invention this back projection technique is changed to select a different value (t') from the corrected projection data set 86. This selection is made as follows:

$$t' = x' \cos\theta + y' \sin\theta \quad [19]$$

where $$x' = (x - \alpha_x)/\beta_x \quad [20]$$

$$y' = (y - \alpha_y)/\beta_y \quad [21]$$

That is, the back projection process is modified by a displacement factor that is determined by the values $\alpha_x$, $\alpha_y$, $\beta_x$ and $\beta_y$. This change is illustrated in FIG. 7 where (x,y) is the pixel in the reference image being reconstructed, (x',y') is the location of the same point in the patient, at the time the projection data was actually acquired, and the attenuation value 89 is the value selected by equation [19]. In other words, the geometric model and the motion parameter D indicate that the attenuation value to be used at the pixel (x,y) from the projection data 86 is the value 89 at t' rather than the attenuation value 87. After the contribution to each pixel in the image has been computed, the system loops at decision block 90 to advance the gantry and acquire and process that data for the next view. When 180° of data have been acquired and processed in this manner, the scan is complete and the image data 85 is displayed at process block 91. The CT numbers in the image data array 85 are scaled and processed in the normal fashion to produce an image of the desired brightness level and range.

The teaching of the present invention is also applicable to fan-beam CT scanners which employ the back projection technique of image reconstruction. As in the preferred embodiment described above, the acquired projection data is corrected by a weighting factor that is determined by the magnification and shift values $\alpha_x$, $\alpha_y$, $\beta_x$ and $\beta_y$, and the back projection process is modified by a displacement factor that is also determined by these same values. The calculation of the weighting factors and displacement factors are different, however, due to the different geometry.

Figure 6:
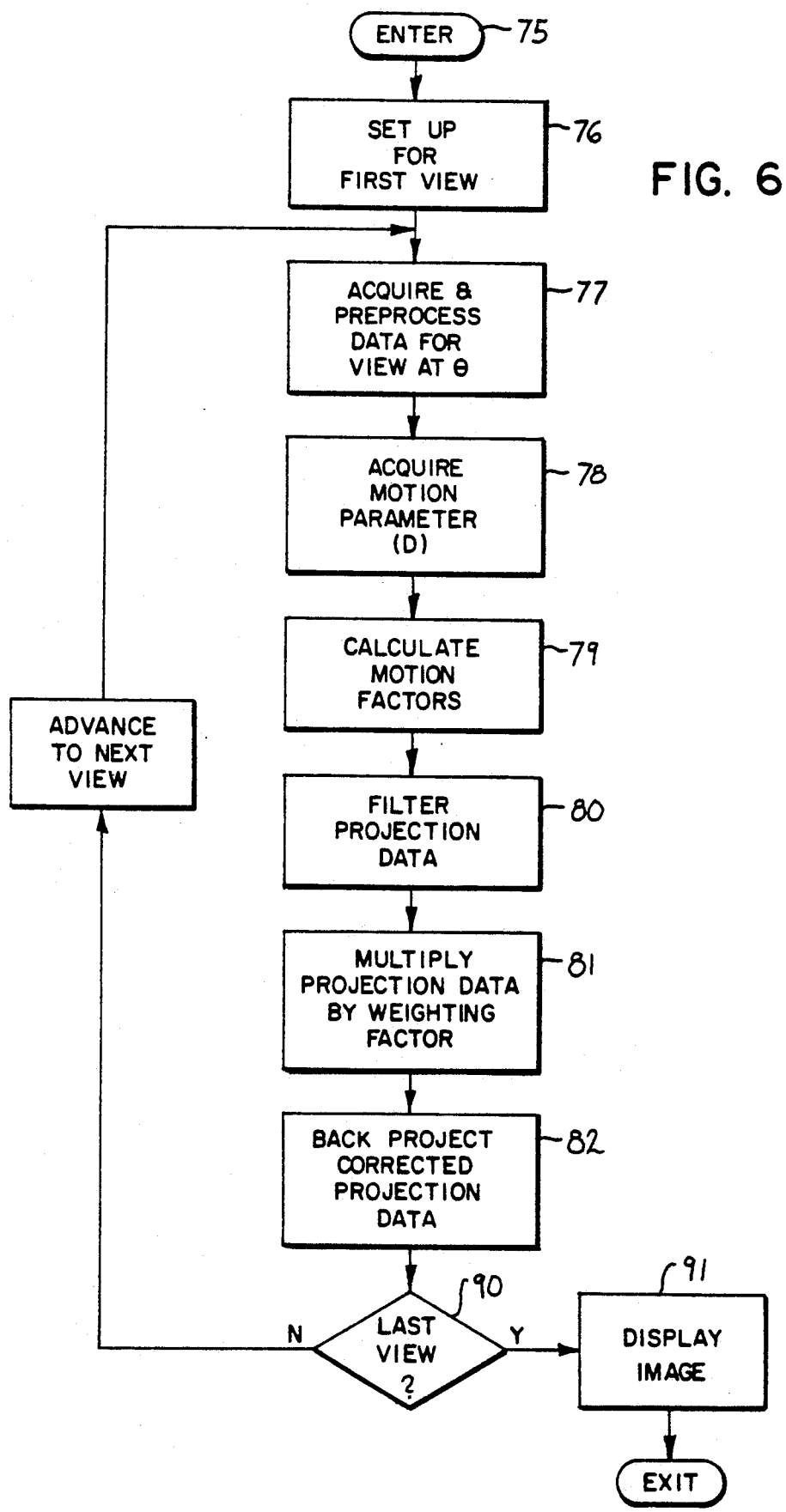
FIG. 6 is a flow chart of the program executed by the CT scanner of FIG. 1 to carry out the preferred embodiment of the invention.

For a flat detector fan-beam reconstruction the weighting factor used in process block 81 in FIG. 6 is as follows:

$$G(S,\alpha) = \left| 1 + \frac{\sin 2(\alpha + \tan^{-1} S/R)}{2} \left[ \frac{\beta'_x}{\beta_x} - \frac{\beta'_y}{\beta_y} \right] \right| \frac{RZ}{2\beta_x \beta_y} \quad [21]$$

where $\alpha$ is the rotational position of the gantry, s is the position of the x-ray detector which is being weighted with respect to the center of the detector array, R is the distance between the x-ray source and the center of the detector array, and $$Z = \sqrt{R^2 + S^2}.$$

In contrast to the parallel beam acquisition, this weighting factor not only varies as a function of gantry position $\alpha$, but also as a function of the location of the detector in the flat array. During the back projection process of block 82 a different formula than equation [18] is used for selecting the proper attenuation value for each pixel (x,y). Many back projection formulas are known in the art such as that described in U.S. Pat. No. 4,812,983 entitled "Method and Means of Correcting For a Shift in the Center of Rotation of a Rotating Fan-Beam CT System" which is encorporated herein by reference. Regardless of the formula used, the displacement factor of the present invention is applied by substituting the values of x' and y' given above in equations [20] and [21] for the values of x and y respectively in the particular back projection formula used.

For a curved detector fan-beam reconstruction the weighting factor used in process block 81 in FIG. 6 is as follows:

$$G(\alpha,\gamma) = \left| 1 + \frac{\sin 2(\alpha + \gamma)}{2} \left[ \frac{\beta'_x}{\beta_x} - \frac{\beta'_y}{\beta_y} \right] \right| \frac{R \cos\gamma}{2\beta_x \beta_y} \quad [22]$$

where $\alpha$ is the rotational position of the gantry, R is the distance between the x-ray source and the central axis of rotation of the gantry, and $\gamma$ is the angle as measured at the x-ray source between the central array detector and the detector whose signal is being weighted. During the back projection process of block 82, the values of x' and y' given above in equations [20] and [21] are substituted for the values of x and y respectively in the formula used for back projection.

While the theory indicates that the weighting factors must be applied to correct the projection data before it is used to reconstruct an image according to the present invention, experimental results have shown that this is not always required. In many cases, a substantial reduction in motion artifacts can be achieved without applying the weighting factor and only applying the displacement factor to the back projection process.

It should be apparent to those skilled in the art that the present invention is applicable to many different back projection reconstruction techniques. Regardless of the back projection technique used, a weighting factor can be calculated for each acquired attenuation value in the data set and the back projection process can be modified by substituting the displacement factors of equations [20] and [21] into the back projection formula. This is true regardless of the modality used to acquire the projection data. Thus, for example, projection data acquired with PET, MRI or SPECT scanners can be corrected for patient motion according to the teachings of the present invention.

It is well-known that in x-ray CT fan-beam reconstruction certain factors can be applied to projection data to diminish the effects of patient motion. While the mathematics suggests that the present invention will not work with such prior methods, experimental results have demonstrated that some improvement is in fact obtained when the present invention is used in combination with such technique.

I claim:

1. A method for producing an image, of a patient, the steps comprising:
    performing a scan in which a plurality of sets of projection data are acquired, each set of projection data being a view of a physical characteristic of the patient as seen from a different projection angle ($\theta$);
    acquiring a motion parameter with each set of acquired projection data, each acquired motion parameter being indicative of the position of the patient as the projection data is acquired; and
    back projecting each set of projection data to produce the image of the patient using a back projection formula which is modified by a displacement factor that has a value which is a function of the acquired motion parameter and a geometric model of patient motion;
    whereby artifacts produced in the image by movement of the patient from view-to-view during the scan are reduced.

2. The method as recited in claim 1 in which the motion parameter acquired with each set of projection data indicates the position of the anterior chest wall of the patient.

3. The method as recited in claim 1 which includes:
    calculating a weighting factor for each set of projection data which is a function of the motion parameter acquired with the projection data and the projection angle ($\theta$); and
    correcting each set of projection data by multiplying the projection data by its associated weighting factor prior to the back projection of the projection data.

4. The method as recited in claim 3 in which the motion parameter acquired with each set of projection data indicates the position of the anterior chest wall of the patient and the weighting factor is calculated using the acquired motion parameter and a reference value which indicates the position of the anterior chest wall of the patient at a point in the patient's respiratory cycle.

5. The method as recited in claim 3 in which the projection data is x-ray attenuation values.

6. The method as recited in claim 5 in which the view-to-view movement of the patient is due to respiration and a weighting factor is calculated based on a geometric model of the motion of the patient's chest cavity during respiration and the acquired motion parameter which indicates the position of the patient's anterior chest wall.

7. The method as recited in claim 6 in which the geometric model of patient motion is given by the formula $$f(x,y) = f(\alpha_x + \beta_x x, \alpha_y + \beta_y y)$$

where $\beta_x$ and $\beta_y$ are magnification factors and $\alpha_x$ and $\alpha_y$ are shift factors which indicate a point about which magnification occurs.

8. The method as recited claim 1 in which the set of projection data is acquired with parallel x-ray beams.

9. The method as recited in claim 1 in which the set of projection data is acquired with a curved array of x-ray detectors that receive a fan-beam of x-rays.

10. The method as recited in claim 1 in which the set of projection data is acquired with a flat array of x-ray detectors that receive a fan-beam of x-rays.

* * * * *